United States Patent
Maki et al.

(10) Patent No.: US 11,951,245 B2
(45) Date of Patent: Apr. 9, 2024

(54) BLOOD PURIFICATION APPARATUS

(71) Applicant: Nikkiso Company Limited, Tokyo (JP)

(72) Inventors: Hideto Maki, Shizuoka (JP); Tomohiro Furuhashi, Shizuoka (JP); Kazuhide Ono, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 474 days.

(21) Appl. No.: 17/225,616

(22) Filed: Apr. 8, 2021

(65) Prior Publication Data

US 2021/0220544 A1    Jul. 22, 2021

Related U.S. Application Data

(63) Continuation of application No. PCT/JP2019/043767, filed on Nov. 7, 2019.

(30) Foreign Application Priority Data

Nov. 8, 2018   (JP) .................................. 2018-210894

(51) Int. Cl.
*A61M 1/16*     (2006.01)
*A61M 1/00*     (2006.01)
*A61M 1/36*     (2006.01)

(52) U.S. Cl.
CPC ............ *A61M 1/69* (2021.05); *A61M 1/1601* (2014.02); *A61M 1/1621* (2014.02);
(Continued)

(58) Field of Classification Search
CPC ........ A61M 1/16; A61M 1/34; A61M 1/3649; A61M 1/36
See application file for complete search history.

(56) References Cited

U.S. PATENT DOCUMENTS

2016/0250405 A1* 9/2016 Kogoshi ............. A61M 1/3649
                                                        210/321.72

FOREIGN PATENT DOCUMENTS

EP       0956080 B1    12/2003
JP       S56-036963 A   4/1981
(Continued)

OTHER PUBLICATIONS

WO-2017073731-A1 Translation (Year: 2017).*
(Continued)

*Primary Examiner* — Walter D. Griffin
*Assistant Examiner* — Cameron J Allen
(74) *Attorney, Agent, or Firm* — Young Basile Hanlon & MacFarlane, P.C.

(57) ABSTRACT

The present teachings provide a blood purification apparatus including a drain-liquid temporary chamber that stores drain liquid drained from a blood purifier that purifies blood of a patient, a first drain-liquid drain line through which the drain liquid flows into the drain-liquid temporary chamber, a second drain-liquid drain line through which the drain liquid stored in the drain-liquid temporary chamber is drained to an outside of the apparatus, a draining unit provided to the second drain-liquid drain line and that drains the drain liquid stored in the drain-liquid temporary chamber to the outside of the apparatus, a remaining-amount-detecting unit that detects an amount of drain liquid remaining in the drain-liquid temporary chamber, a judging unit that judges whether or not a reference remaining amount is reached by the drain liquid in the drain-liquid temporary chamber from a result of detection by the remaining-amount-detecting unit, and a control unit that controls the draining unit. The control unit executes a draining process in which the draining unit is controlled such that the drain liquid in the drain-liquid temporary chamber is drained to the outside of the appara-
(Continued)

tus. The draining process is ended if it is judged by the judging unit that the reference remaining amount is reached by the drain liquid in the drain-liquid temporary chamber.

8 Claims, 8 Drawing Sheets

(52) U.S. Cl.
CPC ........ *A61M 1/3607* (2014.02); *A61M 1/3621* (2013.01); *A61M 2205/3382* (2013.01)

(56) References Cited

FOREIGN PATENT DOCUMENTS

| | | | |
|---|---|---|---|
| JP | 2006-095184 A | 4/2006 | |
| JP | 2012-200275 A | 10/2012 | |
| WO | 2004/014463 A1 | 2/2004 | |
| WO | 2016-104720 A1 | 6/2016 | |
| WO | WO-2017073731 A1 * | 5/2017 | .......... A61M 1/3627 |

OTHER PUBLICATIONS

Potentially related Patent application filed Apr. 8, 2021, entitled "Blood Purification Apparatus", published as WO2020096017A1.
European Search Report for Application No. 19 882 467.4, dated Apr. 26, 2022, 13 pgs.

* cited by examiner

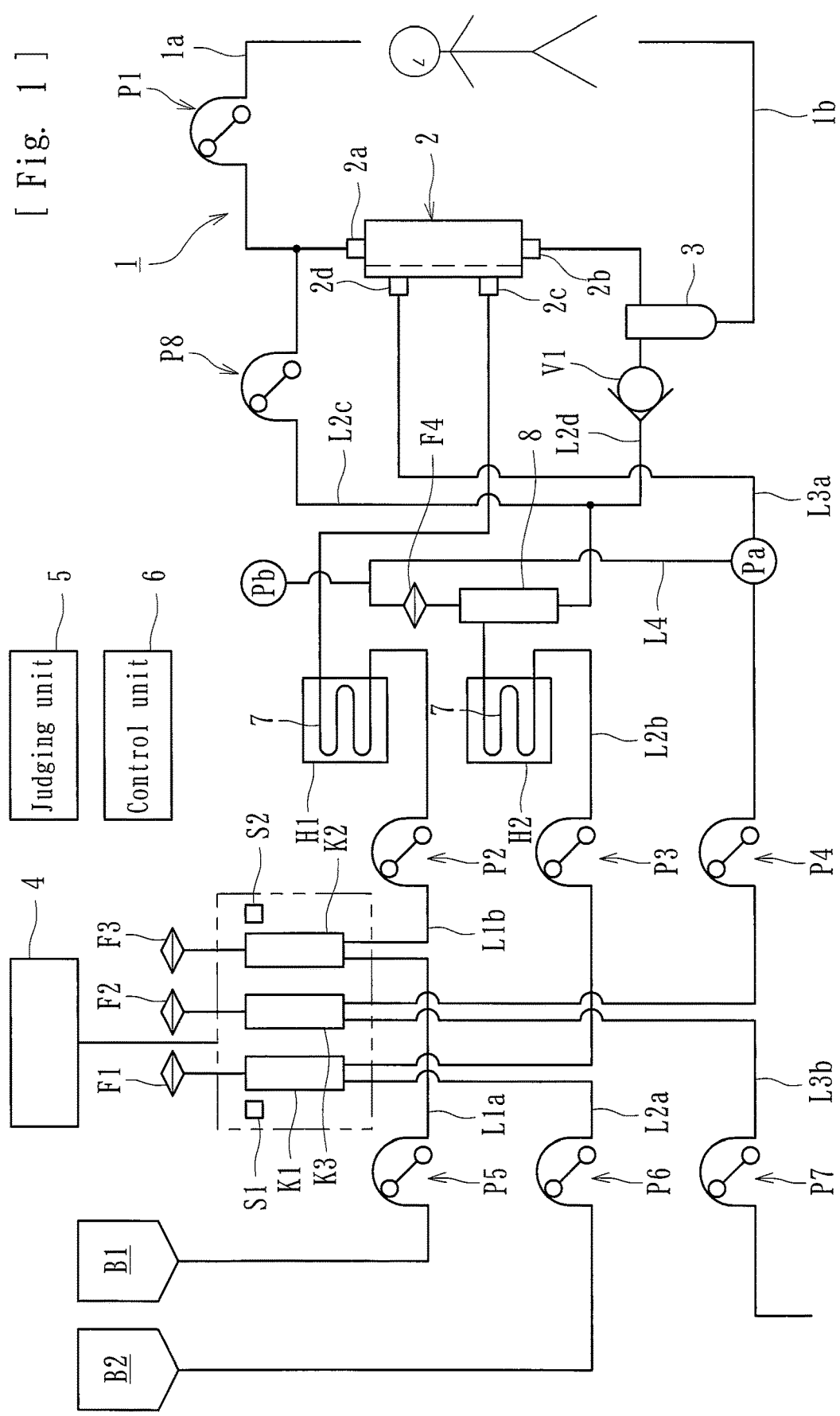
[Fig. 1]

[Fig. 2]
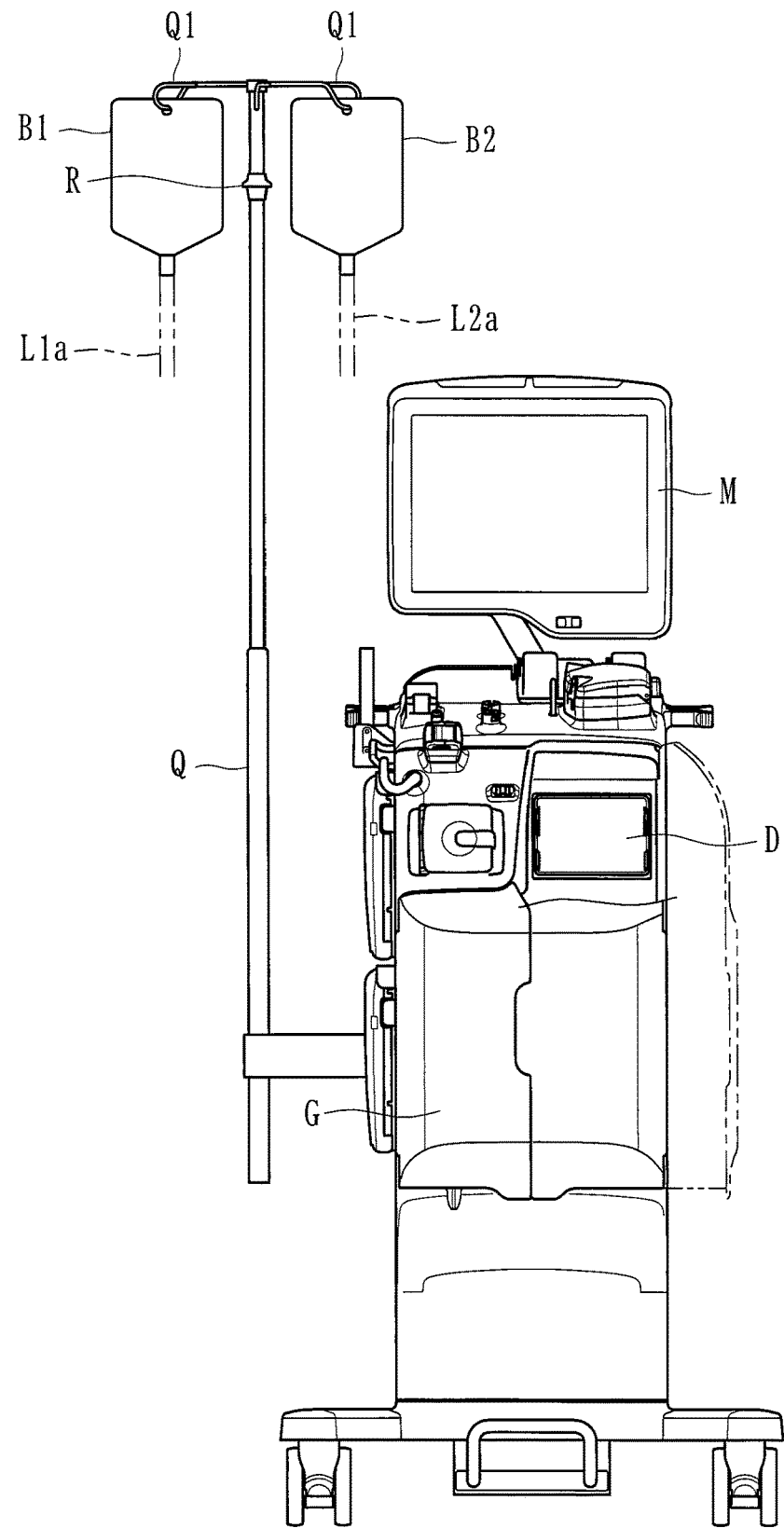

[Fig. 3]
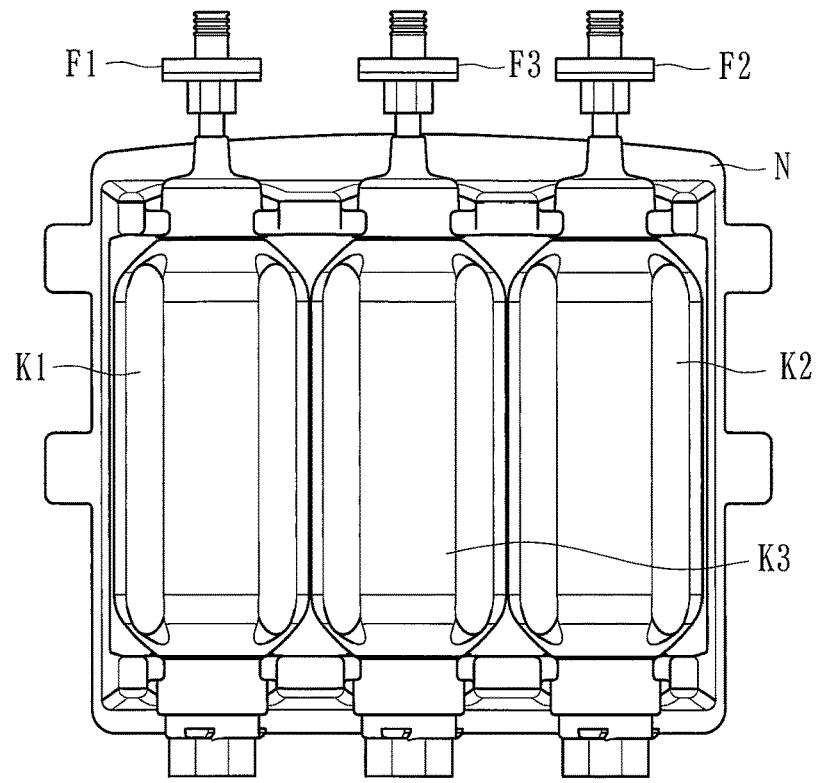
[Fig. 4]
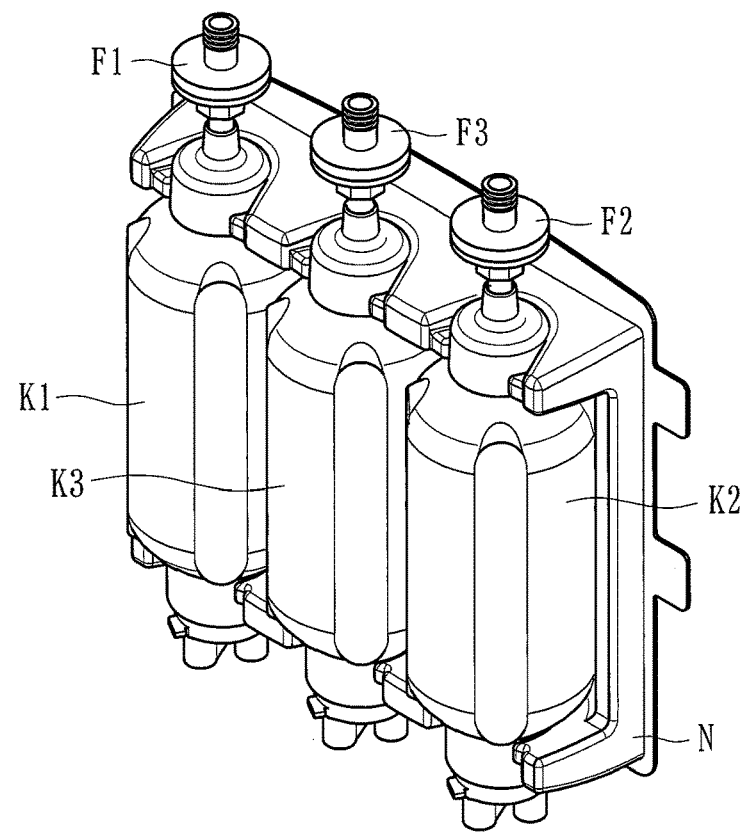

[ Fig. 5 ]
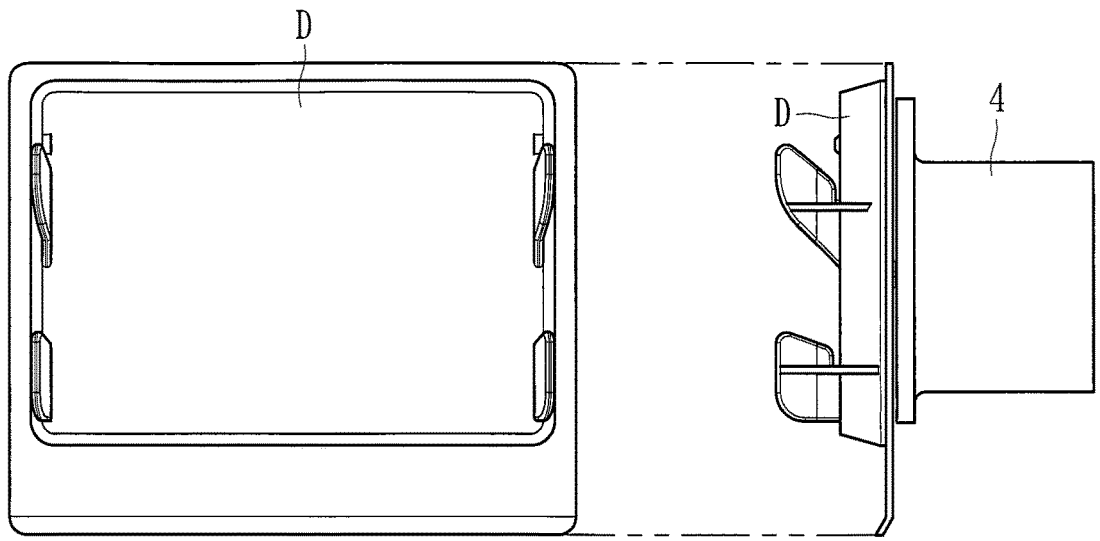
[ Fig 6 ]
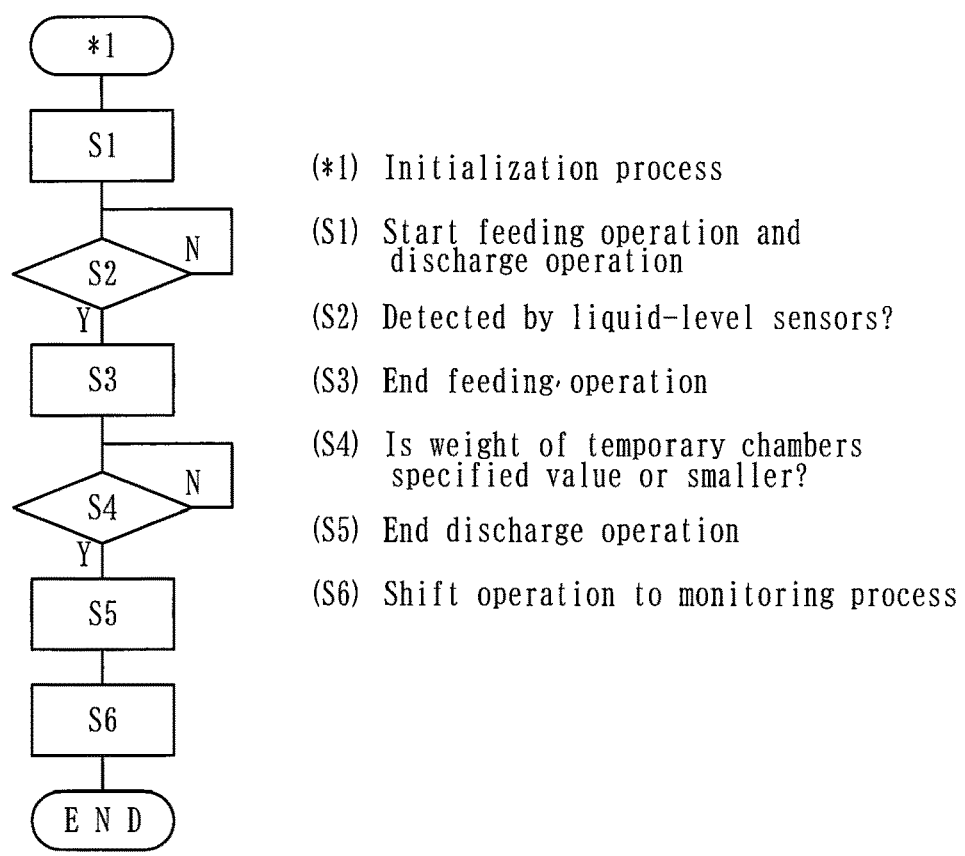
(*1) Initialization process
(S1) Start feeding operation and discharge operation
(S2) Detected by liquid-level sensors?
(S3) End feeding operation
(S4) Is weight of temporary chambers specified value or smaller?
(S5) End discharge operation
(S6) Shift operation to monitoring process

[ Fig. 7 ]
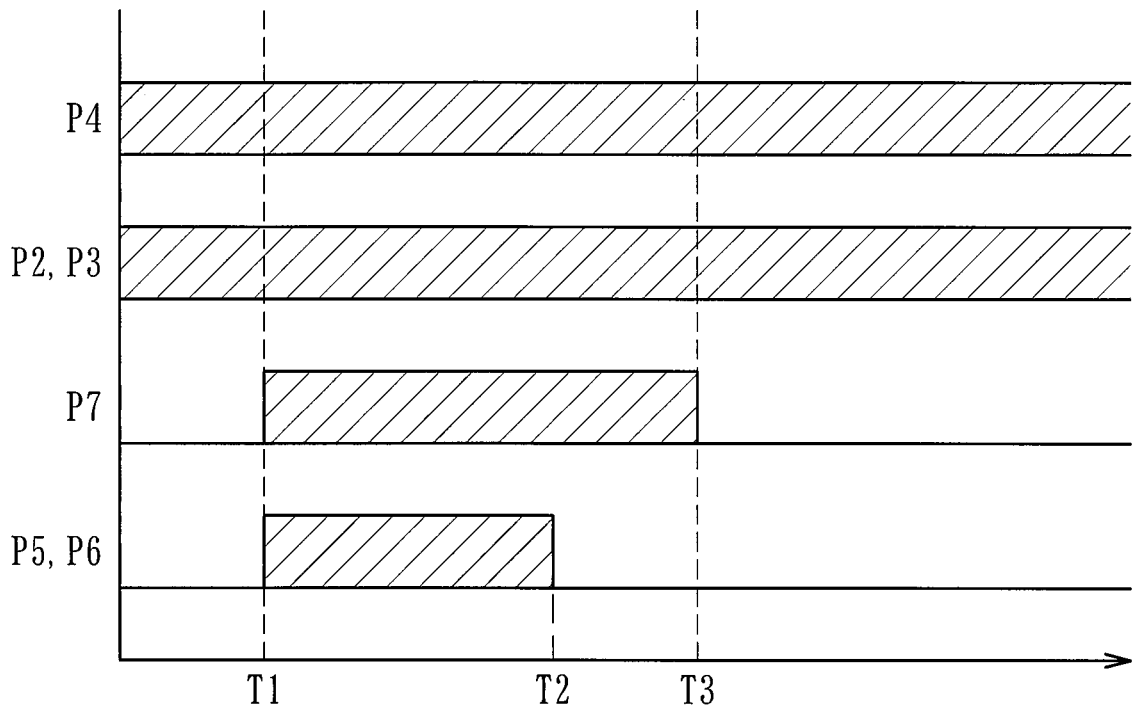
[ Fig 8 ]
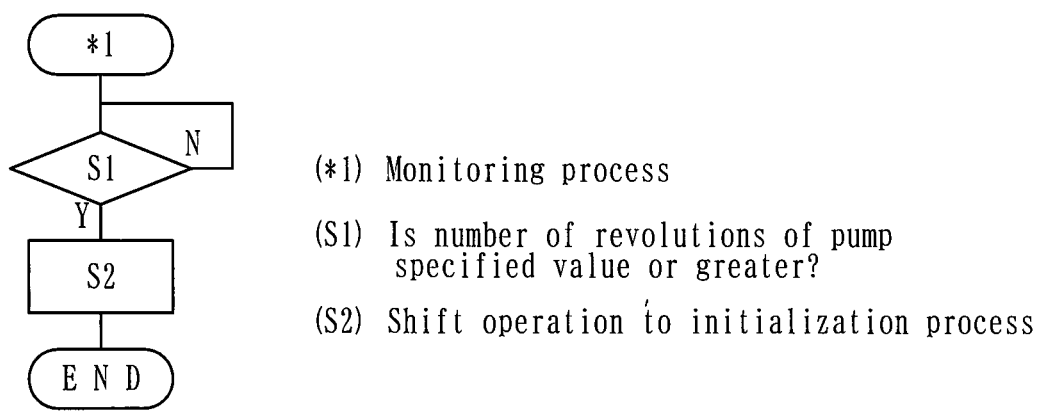
(∗1) Monitoring process
(S1) Is number of revolutions of pump specified value or greater?
(S2) Shift operation to initialization process

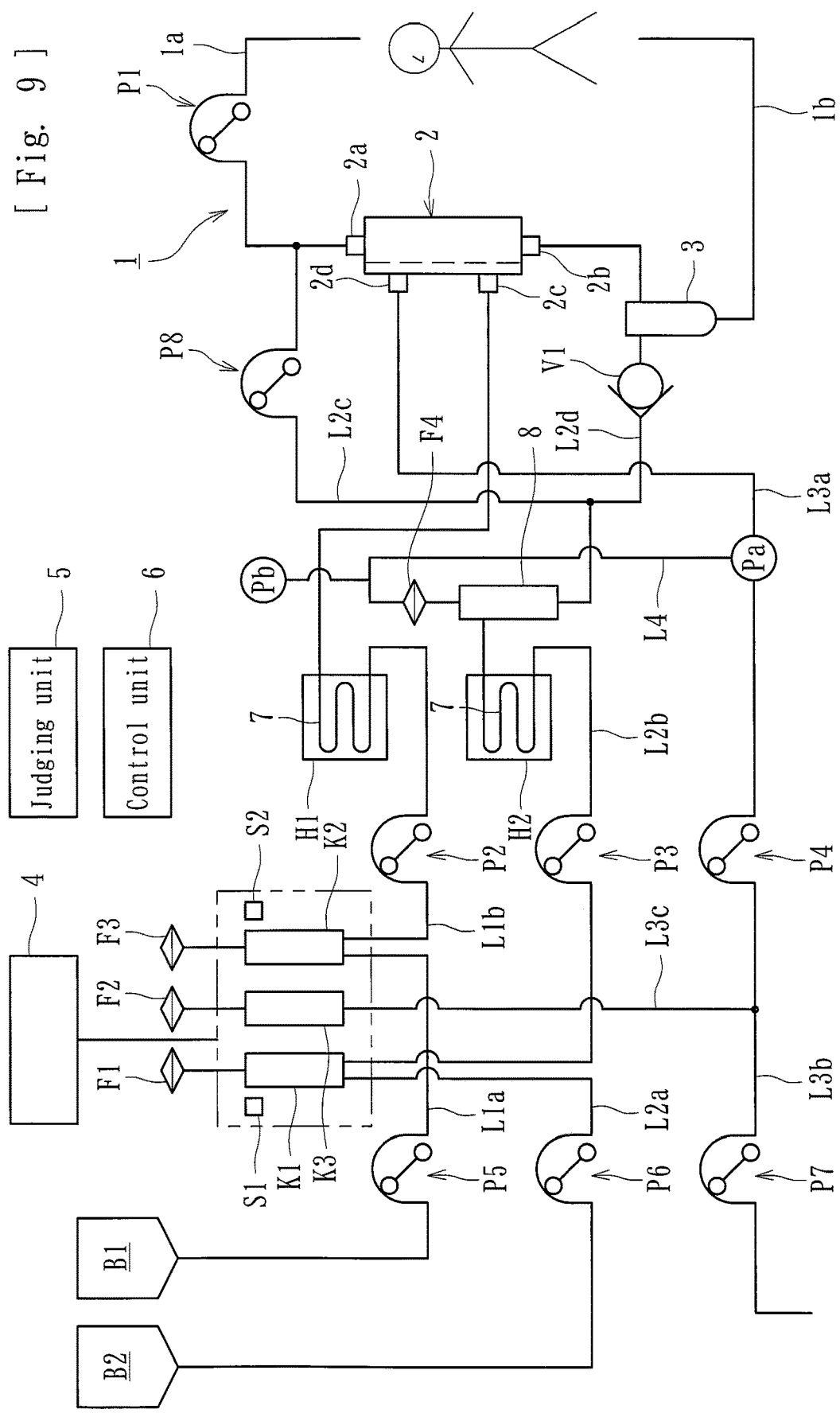
[Fig. 9]

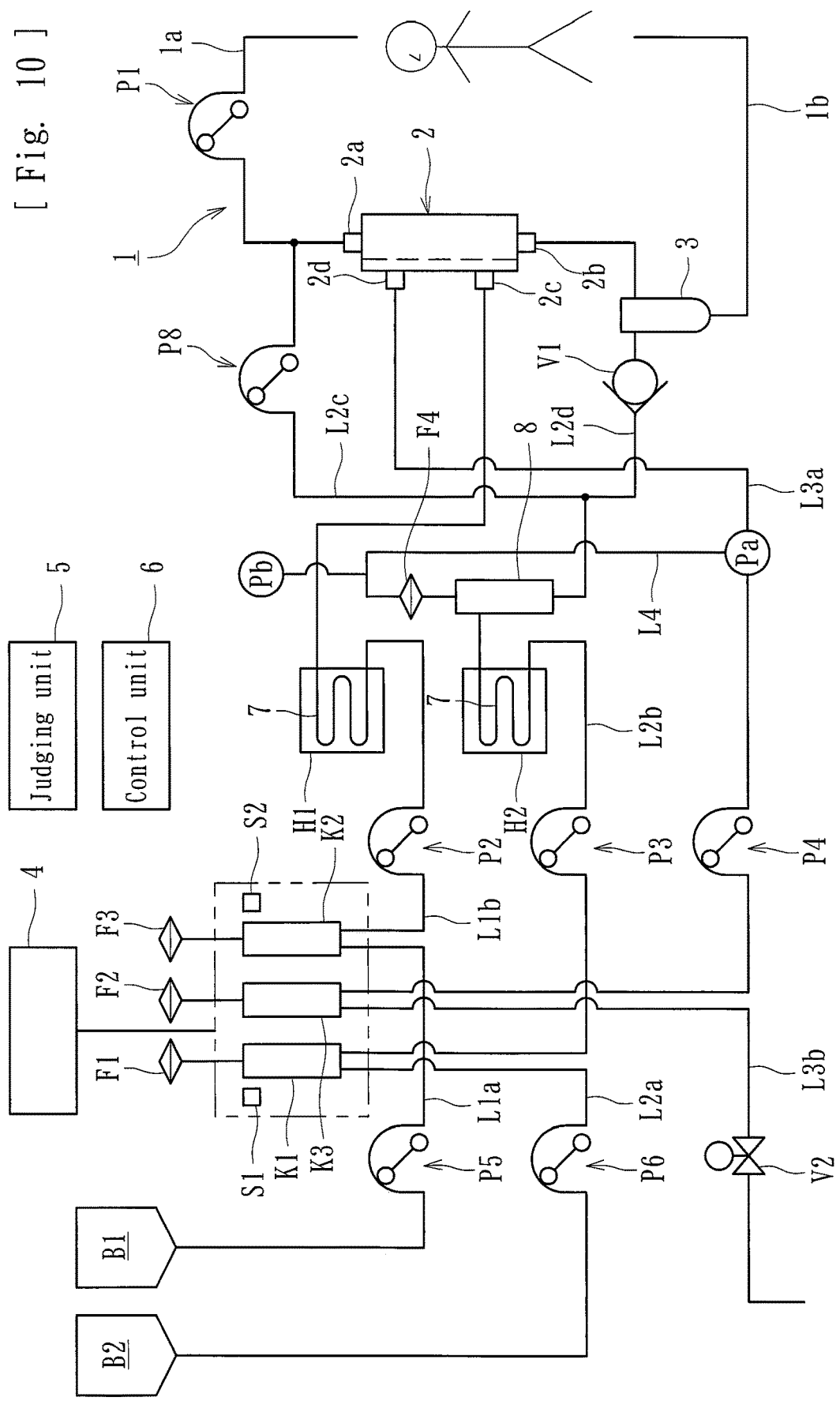
[Fig. 10]

[ Fig 11 ]
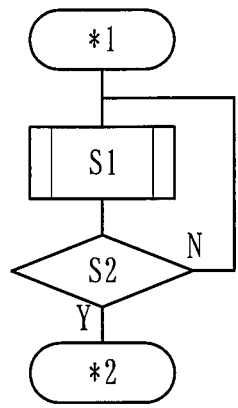
(∗1) Start draining process
(S1) Waste-Liquid-Controlling step
(S2) Any air or specified value or smaller?
(∗2) End draining process
[ Fig 12 ]
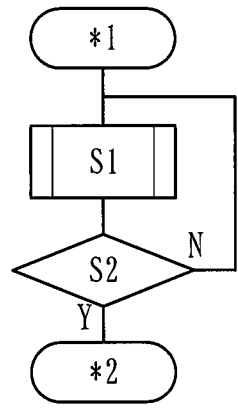
(∗1) Start draining process
(S1) Waste-Liquid-Controlling step
(S2) Calculate remaining amount
(S3) Remaining amount < Specified amount ?
(∗2) End draining process

BLOOD PURIFICATION APPARATUS

CROSS-REFERENCE TO RELATED APPLICATION(S)

This application is a continuation of International Application No. PCT/JP2019/043767, filed on Nov. 7, 2019, which claims priority to Japanese Application No. 2018-210894, filed on Nov. 8, 2018, the entire disclosures of which are hereby incorporated by reference.

FIELD

The present teachings relate to a blood purification apparatus for purifying blood of a patient while causing the blood to extracorporeally circulate.

BACKGROUND

In general, a blood purification apparatus for giving dialysis treatment includes an arterial blood circuit and a venous blood circuit that form a blood circuit for causing blood of a patient to extracorporeally circulate, a blood purifier for purifying the blood extracorporeally circulating through the blood circuit, and an apparatus body provided with various treatment devices, such as a blood pump, for performing blood purification treatment with the blood circuit and the blood purifier. The arterial blood circuit and the venous blood circuit are each provided with a vascular access catheter or a puncture needle (an arterial puncture needle or a venous puncture needle) that is attachable to a distal end thereof.

For example, after the patient is punctured with the arterial puncture needle and the venous puncture needle, the blood pump is activated. Thus, blood of the patient flows through the arterial blood circuit and the venous blood circuit. In this flowing process, the blood is purified by the blood purifier. In dialysis treatment, a dialysate introduction line for introducing dialysate into the blood purifier and a drain-liquid drain line for draining drain liquid from the blood purifier are connected to the blood purifier.

Methods established for blood purification treatment include hemodialysis (HD) in which dialysate is made to flow through dialysate flow routes provided in the blood purifier and substances in the blood are removed by the effect of diffusion through blood purification membranes, hemofiltration (HF) in which water and substances in the blood are removed by the effect of ultrafiltration pressure generated in the blood purifier and an amount of substitution fluid that is equal to the amount of water removed is infused into the blood, and hemodiafiltration (HDF) in which hemodialysis (HD) and hemofiltration (HF) are performed simultaneously. In particular, when blood purification treatment is given to a patient having a disease such as acute renal failure, the treatment method needs to be switched among hemodialysis (HD), hemofiltration (HF), and hemodiafiltration (HDF) during a series of treatment steps in accordance with the patient's condition.

To meet the above demand, in a known art, an initialization process in which drain liquid stored in a drain-liquid temporary chamber is drained, and a monitoring process in which the drain liquid stored in the drain-liquid temporary chamber is weighed with a weighing device are executed. Since the initialization process is executed, the drain liquid can be prevented from spilling from the drain-liquid temporary chamber. Such a technique is not disclosed by any publicly available patent literature. Therefore, no patent literature is cited herein.

SUMMARY

In a blood purification apparatus according to the above known art, all of the drain liquid in the drain-liquid temporary chamber is drained in the initialization process. Therefore, when drain liquid is stored in the drain-liquid temporary chamber again, air tends to be introduced thereinto. Such a configuration makes it difficult to accurately weigh the drain liquid in the drain-liquid temporary chamber in the monitoring process.

The present invention has been conceived in view of the above circumstances and provides a blood purification apparatus in which introduction of air into a drain-liquid temporary chamber that may occur with the execution of an initialization process can be suppressed.

Variation 1 may comprise, a blood purification apparatus including a drain-liquid temporary chamber that stores drain liquid drained from a blood purifier that purifies blood of a patient, a first drain-liquid drain line through which the drain liquid flows into the drain-liquid temporary chamber, a second drain-liquid drain line through which the drain liquid stored in the drain-liquid temporary chamber is drained to an outside of the apparatus, a draining unit provided to the second drain-liquid drain line and that drains the drain liquid stored in the drain-liquid temporary chamber to the outside of the apparatus, a remaining-amount-detecting unit that detects an amount of drain liquid remaining in the drain-liquid temporary chamber, a judging unit that judges whether or not a reference remaining amount is reached by the drain liquid in the drain-liquid temporary chamber from a result of detection by the remaining-amount-detecting unit, and a control unit that controls the draining unit. Furthermore, the control unit executes a draining process in which the draining unit is controlled such that the drain liquid in the drain-liquid temporary chamber is drained to the outside of the apparatus. Furthermore, the draining process is ended if it is judged by the judging unit that the reference remaining amount is reached by the drain liquid in the drain-liquid temporary chamber.

Variation 2 may comprise, the blood purification apparatus according to variation 1, the control unit further executes a monitoring process in which the amount of drain liquid in the drain-liquid temporary chamber is monitored by the remaining-amount-detecting unit. Furthermore, operation is shifted from the draining process to the monitoring process if it is judged by the judging unit that the reference remaining amount is reached by the drain liquid in the drain-liquid temporary chamber.

Variation 3 may comprise, the blood purification apparatus according to variation 1 or 2, the control unit alternately executes the draining process and the monitoring process.

Variation 4 may comprise, the blood purification apparatus according to any of variations 1 to 3 further includes a feeding-liquid storage that stores, as feeding liquid, dialysate to be fed to the blood purifier or substitution fluid to be fed through the blood purifier to a blood circuit through which the blood of the patient circulates, a feeding-liquid temporary chamber that stores the feeding liquid received from the feeding-liquid storage, and a feeding-liquid introduction line through which the feeding liquid stored in the feeding-liquid storage flows into the feeding-liquid temporary chamber. Furthermore, the remaining-amount-detecting unit includes a weighing device that measures a total weight of the feeding-liquid temporary chamber and the drain-liquid temporary chamber. Furthermore, the draining process is an initialization process in which the amount of drain liquid in the drain-liquid temporary chamber and an amount of feeding liquid in the feeding-liquid temporary chamber are initialized by continuing the draining until the reference remaining amount is reached by the drain liquid in the drain-liquid temporary chamber while continuing the feeding until a reference feeding amount is reached by the feeding liquid in the feeding-liquid temporary chamber. Furthermore, the judging unit judges whether or not the reference remaining amount is reached by the drain liquid in the drain-liquid temporary chamber in the initialization process from a result of measurement by the weighing device while the feeding of the feeding liquid to the feeding-liquid temporary chamber is stopped.

Variation 5 may comprise, the blood purification apparatus according to variation 4, the remaining-amount-detecting unit further includes a liquid-level sensor that detects a surface of the feeding liquid in the feeding-liquid temporary chamber. Furthermore, the judging unit judges whether or not the reference feeding amount is reached by the feeding liquid in the feeding-liquid temporary chamber in the initialization process from a result of detection by the liquid-level sensor. Furthermore, the control unit stops the feeding of the feeding liquid to the feeding-liquid temporary chamber if it is judged by the judging unit that the reference feeding amount is reached by the feeding liquid in the feeding-liquid temporary chamber in the initialization process.

Variation 6 may comprise, the blood purification apparatus according to any of variations 1 to 3 further includes a feeding-liquid storage that stores, as feeding liquid, dialysate to be fed to the blood purifier or substitution fluid to be fed through the blood purifier to a blood circuit through which the blood of the patient circulates, a feeding-liquid temporary chamber that stores the feeding liquid received from the feeding-liquid storage, and a feeding-liquid introduction line through which the feeding liquid stored in the feeding-liquid storage flows into the feeding-liquid temporary chamber. Furthermore, the remaining-amount-detecting unit includes a weighing device that measures a total weight of the feeding-liquid temporary chamber and the drain-liquid temporary chamber. Furthermore, the draining process is an initialization process in which the amount of drain liquid in the drain-liquid temporary chamber and an amount of feeding liquid in the feeding-liquid temporary chamber are initialized by continuing the draining until the reference remaining amount is reached by the drain liquid in the drain-liquid temporary chamber while continuing the feeding until a reference feeding amount is reached by the feeding liquid in the feeding-liquid temporary chamber. Furthermore, the judging unit judges whether or not the reference remaining amount is reached by the drain liquid in the drain-liquid temporary chamber in the initialization process from a result of measurement by the weighing device while the amount of feeding liquid in the feeding-liquid temporary chamber is maintained at a constant value.

Variation 7 may comprise, the blood purification apparatus according to any of variations 1 to 6, the draining unit is provided as a drain-liquid transfer pump that drains the drain liquid stored in the drain-liquid temporary chamber to the outside of the apparatus by transferring the drain liquid.

Variation 8 may comprise, the blood purification apparatus according to variation 3 further includes a drain-liquid drain pump provided to the first drain-liquid drain line and that delivers dialysate from the blood purifier to the drain-liquid temporary chamber. Furthermore, the draining unit is provided as a drain-liquid transfer pump that drains the drain liquid stored in the drain-liquid temporary chamber to the outside of the apparatus by transferring the drain liquid. Furthermore, if a total amount of flow generated by the drain-liquid drain pump in a previous monitoring process is reached by a total amount of flow generated by the drain-liquid transfer pump in the draining process, the control unit shifts the operation to the monitoring process.

Variation 9 may comprise, the blood purification apparatus according to variation 7, the drain-liquid transfer pump is a peristaltic pump that delivers liquid by squeezing a flexible tube forming a flow route for the drain liquid.

Variation 10 may comprise, in the blood purification apparatus according to any of variations 1 to 9, the draining unit is provided to the second drain-liquid drain line, the second drain-liquid drain line extending from a bottom of the drain-liquid temporary chamber.

Variation 1 may comprise, the draining process is executed in which the draining unit is controlled such that the drain liquid in the drain-liquid temporary chamber is drained to the outside of the apparatus. Furthermore, the draining process is ended if it is judged by the judging unit that the reference remaining amount is reached by the drain liquid in the drain-liquid temporary chamber. Therefore, introduction of air into the drain-liquid temporary chamber that may occur with the execution of the draining process can be suppressed.

Variation 2 may comprise, the monitoring process is further executed in which the amount of drain liquid in the drain-liquid temporary chamber is monitored by the remaining-amount-detecting unit. Furthermore, the operation is shifted from the draining process to the monitoring process if it is judged by the judging unit that the reference remaining amount is reached by the drain liquid in the drain-liquid temporary chamber. Therefore, smooth shifting from the draining process to the monitoring process can be achieved.

Variation 3 may comprise, the control unit alternately executes the draining process and the monitoring process. Therefore, smooth repetition of the draining process and the monitoring process can be achieved.

Variation 4 may comprise, the blood purification apparatus further includes the feeding-liquid storage that stores, as the feeding liquid, the dialysate to be fed to the blood purifier or the substitution fluid to be fed through the blood purifier to the blood circuit through which the blood of the patient circulates, the feeding-liquid temporary chamber that stores the feeding liquid received from the feeding-liquid storage, and the feeding-liquid introduction line through which the feeding liquid stored in the feeding-liquid storage flows into the feeding-liquid temporary chamber. Furthermore, the remaining-amount-detecting unit includes the weighing device that measures the total weight of the feeding-liquid temporary chamber and the drain-liquid temporary chamber. Furthermore, the draining process is the initialization process in which the amount of drain liquid in the drain-liquid temporary chamber and the amount of feeding liquid in the feeding-liquid temporary chamber are initialized by continuing the draining until the reference remaining amount is reached by the drain liquid in the drain-liquid temporary chamber while continuing the feeding until the reference feeding amount is reached by the feeding liquid in the feeding-liquid temporary chamber. Furthermore, the judging unit judges whether or not the reference remaining amount is reached by the drain liquid in the drain-liquid temporary chamber in the initialization process from the result of measurement by the weighing device while the feeding of the feeding liquid to the feeding-liquid temporary chamber is stopped. Therefore, in the initialization process, a situation where the drain-liquid temporary chamber has been initialized can be grasped correctly.

Variation 5 may comprise, the remaining-amount-detecting unit further includes the liquid-level sensor that detects the surface of the feeding liquid in the feeding-liquid temporary chamber. Furthermore, the judging unit judges whether or not the reference feeding amount is reached by the feeding liquid in the feeding-liquid temporary chamber in the initialization process from the result of detection by the liquid-level sensor. Furthermore, the control unit stops the feeding of the feeding liquid to the feeding-liquid temporary chamber if it is judged by the judging unit that the reference feeding amount is reached by the feeding liquid in the feeding-liquid temporary chamber in the initialization process. Therefore, in the initialization process, a situation where the feeding-liquid temporary chamber have become full can be grasped correctly, and the situation where the drain-liquid temporary chamber has been initialized can be grasped correctly.

Variation 6 may comprise, the judging unit judges whether or not the reference remaining amount is reached by the drain liquid in the drain-liquid temporary chamber in the initialization process from the result of measurement by the weighing device while the amount of feeding liquid in the feeding-liquid temporary chamber is maintained at a constant value. Specifically, since the amount of feeding liquid to be fed to the feeding-liquid temporary chamber and the amount of feeding liquid to be discharged therefrom are made substantially the same, the liquid level (the amount of liquid) in the feeding-liquid temporary chamber can be maintained at a constant level. Therefore, even with a weighing device that measures the total weight of the feeding-liquid temporary chamber and the drain-liquid temporary chamber, the amount of liquid remaining in the drain-liquid temporary chamber can be grasped, if factors that change the weight of the feeding-liquid temporary chamber are ignored.

Variation 7 may comprise, the draining unit is provided as the drain-liquid transfer pump that drains the drain liquid stored in the drain-liquid temporary chamber to the outside of the apparatus by transferring the drain liquid. Therefore, smooth draining of the drain liquid from the drain-liquid temporary chamber in the initialization process can be achieved. Furthermore, if the flow rate of the drain-liquid transfer pump is controlled, the duration of draining the drain liquid can be adjusted arbitrarily.

Variation 8 may comprise, the blood purification apparatus further includes the drain-liquid drain pump provided to the first drain-liquid drain line and that delivers the dialysate from the blood purifier to the drain-liquid temporary chamber. Furthermore, the draining unit is provided as the drain-liquid transfer pump that drains the drain liquid stored in the drain-liquid temporary chamber to the outside of the apparatus by transferring the drain liquid. Furthermore, if the total amount of flow generated by the drain-liquid drain pump in the previous monitoring process is reached by the total amount of flow generated by the drain-liquid transfer pump in the draining process, the control unit shifts the operation to the monitoring process. Therefore, in combination with the weight condition, the situation where the drain-liquid temporary chamber has been initialized can be grasped more accurately.

Variation 9 may comprise, the drain-liquid transfer pump is a peristaltic pump that delivers liquid by squeezing the flexible tube forming the flow route for the drain liquid. Therefore, the second drain-liquid drain line can be closed by the drain-liquid transfer pump, with no need to provide any separate clamp unit or the like.

Variation 10 may comprise, the draining unit is provided to the second drain-liquid drain line extending from the bottom of the drain-liquid temporary chamber. Therefore, the error in the measurement by the measuring unit can be made smaller than in a case where the drain-liquid transfer pump is provided to another flow route extending from the top of the drain-liquid temporary chamber.

BRIEF DESCRIPTION OF THE DRAWINGS

FIG. 1 is a schematic diagram of a blood purification apparatus according to an embodiment of the present invention.

FIG. 2 illustrates the appearance of the blood purification apparatus in front view (with temporary chambers yet to be attached).

FIG. 3 is a front view of the temporary chambers included in the blood purification apparatus.

FIG. 4 is a perspective view of the temporary chambers.

FIG. 5 includes a front view and a side view of an attaching unit included in the blood purification apparatus and to which the temporary chambers are attached.

FIG. 6 is a flow chart of a control sequence (an initialization process) executed by a control unit of the blood purification apparatus.

FIG. 7 is a timing chart illustrating the timing of activating pumps included in the blood purification apparatus.

FIG. 8 is a flow chart of a control sequence (a monitoring process) executed by the control unit of the blood purification apparatus.

FIG. 9 is a schematic diagram of a blood purification apparatus according to another embodiment of the present invention (a drain-liquid temporary chamber is provided with a single flow route).

FIG. 10 is a schematic diagram of a blood purification apparatus according to yet another embodiment of the present invention (including an electromagnetic valve as a draining unit).

FIG. 11 is a flow chart of a control sequence executed by a blood purification apparatus according to yet another embodiment of the present invention.

FIG. 12 is a flow chart of a control sequence executed by a blood purification apparatus according to yet another embodiment of the present invention.

DETAILED DESCRIPTION

Embodiments of the present invention will now be described specifically with reference to the drawings.

A blood purification apparatus according to an embodiment is applied to a hemodialysis apparatus for purifying blood of a patient while causing the blood to extracorporeally circulate. As illustrated in FIGS. 1 to 3, the apparatus includes a blood circuit 1 including an arterial blood circuit 1a and a venous blood circuit 1b; a dialyzer 2 (a blood purifier) provided between the arterial blood circuit 1a and the venous blood circuit 1b and that purifies blood flowing through the blood circuit 1; a first dialysate introduction line L1a and a second dialysate introduction line L1b; a first substitution line L2a and a second substitution line L2b; a pre-substitution line L2c and a post-substitution line L2d; a first drain-liquid drain line L3a and a second drain-liquid drain line L3b; a blood pump P1; a dialysate introduction pump P2; a first substitution pump P3; a drain-liquid drain pump P4; a dialysate transfer pump P5; a substitution-fluid transfer pump P6; a drain-liquid transfer pump P7; a second substitution pump P8; an attaching unit D to which a substitution-fluid temporary chamber K1, a dialysate temporary chamber K2, and a drain-liquid temporary chamber K3 are attachable; a weighing device 4; a judging unit 5; a control unit 6; and a first heating device H1 and a second heating device H2.

Dialysate to be fed to the dialyzer 2 and substitution fluid to be fed to the blood circuit 1 each serve as feeding liquid according to the present invention. A dialysate bag B1 and a substitution-fluid bag B2 each serve as a feeding-liquid storage that stores the feeding liquid. The substitution-fluid temporary chamber K1 and the dialysate temporary chamber K2 each serve as a feeding-liquid temporary chamber according to the present invention. The weighing device 4 and liquid-level sensors (S1 and S2) each serve as a measuring unit (remaining-amount-detecting unit) according to the present invention. The first dialysate introduction line L1a serves as a feeding-liquid introduction line according to the present invention. Reference signs Pa and Pb given in the drawings each denote a pressure sensor. The blood pump P1, the dialysate introduction pump P2, the first substitution pump P3, the drain-liquid drain pump P4, the dialysate transfer pump P5, the substitution-fluid transfer pump P6, the drain-liquid transfer pump P7, and the second substitution pump P8 according to the present embodiment are each a peristaltic pump that delivers liquid by squeezing a flexible tube forming a flow route.

The arterial blood circuit 1a and the venous blood circuit 1b are provided at distal ends thereof with respective connectors, through which an arterial puncture needle and a venous puncture needle (not illustrated) are connectable thereto. When the blood pump P1 is activated while a patient is punctured with the arterial puncture needle connected to the distal end of the arterial blood circuit 1a and the venous puncture needle connected to the distal end of the venous blood circuit 1b, blood of the patient can be made to extracorporeally circulate through the blood circuit 1.

Specifically, when the blood pump P1 is activated while the patient is punctured with the arterial puncture needle and the venous puncture needle, the patient's blood flows through the arterial blood circuit 1a and reaches the dialyzer 2, where the blood is purified. Then, the blood flows through the venous blood circuit 1b and returns into the patient's body. In this specification, a side on which the puncture needle for blood removal (blood collection) is provided is referred to as the "arterial" side, and a side on which the puncture needle for blood return is provided is referred to as the "venous" side. The "arterial" side and the "venous" side are not defined in accordance with which of the artery and the vein is to be the object of puncture.

The venous blood circuit 1b is provided with an air-trap chamber 3 at a halfway position thereof. The blood that extracorporeally circulates through the blood circuit 1 undergoes bubble removal in the air-trap chamber 3 and then returns into the patient. As an alternative to the embodiment in which a blood vessel of the patient is punctured with the arterial puncture needle and the venous puncture needle, the following may be taken: an embodiment in which a double-lumen catheter is inserted into the subclavian vein or the femoral vein of the patient, an embodiment in which a double-lumen catheter is inserted into a blood vessel in an arm of the patient, or the like.

The dialyzer 2 has a blood introduction port 2a through which the blood is to be introduced thereinto, a blood delivery port 2b through which the blood is to be delivered therefrom, a dialysate introduction port 2c through which the dialysate is to be introduced thereinto, a dialysate delivery port 2d through which the dialysate is to be delivered therefrom, blood flow routes (not illustrated) extending between the blood introduction port 2a and the blood delivery port 2b and through which the blood is to flow, dialysate flow routes (not illustrated) extending between the dialysate introduction port 2c and the dialysate delivery port 2d and through which the dialysate is to flow, and blood purification membranes (not illustrated) separating the blood flow routes from the dialysate flow routes and through which the blood flowing in the blood flow routes is to be purified.

More specifically, the dialyzer 2 has the blood introduction port 2a, the blood delivery port 2b, the dialysate introduction port 2c, and the dialysate delivery port 2d all projecting from a housing thereof. The arterial blood circuit 1a is connected to the blood introduction port 2a. The venous blood circuit 1b is connected to the blood delivery port 2b. The second dialysate introduction line L1b is connected to the dialysate introduction port 2c. The first drain-liquid drain line L3a is connected to the dialysate delivery port 2d. For efficient dialysis treatment, the blood introduction port 2a as the inlet for the blood and the dialysate introduction port 2c as the inlet for the dialysate are positioned on the opposite sides in the vertical direction, so that the dialysate flows in a direction opposite to the direction in which the blood flows through the blood flow routes.

The dialyzer 2 houses a plurality of hollow fiber membranes formed of hollow fibers, serving as blood purification membranes for purifying the blood. Specifically, spaces inside the respective blood purification membranes formed of the hollow fibers serve as the blood flow routes, and spaces between the housing and the hollow fibers serve as the dialysate flow routes. The blood purification membranes as the hollow fiber membranes each have a number of microscopic holes (pores) extending therethrough from the outer surface to the inner surface. Impurities and the like contained in the blood flowing in the blood flow routes are allowed to permeate (to be filtered) through the hollow fiber membranes into the dialysate flowing in the dialysate flow routes.

The first dialysate introduction line L1a is made of a flexible tube allowing the dialysate stored in the dialysate bag B1 (a dialysate storage) to flow into the dialysate temporary chamber K2. The first dialysate introduction line L1a has one end connected to the bottom of the dialysate bag B1 (the dialysate storage), and the other end connected to the bottom of the dialysate temporary chamber K2. The dialysate bag B1 stores a predetermined amount of dialysate to be fed to the dialyzer 2. As illustrated in FIGS. 2 and 3, the dialysate bag B1 is supported at a predetermined height position by a supporting unit Q attached to an apparatus body. The dialysate temporary chamber K2 stores the dialysate received from the dialysate bag B1 (the dialysate storage) and is a case with a smaller capacity than the dialysate bag B1.

The first dialysate introduction line L1a is provided with the dialysate transfer pump P5, which is a peristaltic pump that delivers liquid by squeezing a flexible tube forming a flow route for the dialysate. When the dialysate transfer pump P5 is activated, a rotor rotates and rollers squeeze the flexible tube in the lengthwise direction. Thus, the dialysate stored in the dialysate bag B1 can be delivered to and stored in the dialysate temporary chamber K2.

The second dialysate introduction line L1b is made of a flexible tube allowing the dialysate stored in the dialysate temporary chamber K2 to flow into the dialyzer 2. The second dialysate introduction line L1b has one end connected to the bottom of the dialysate temporary chamber K2, and the other end connected to the dialysate introduction port 2c of the dialyzer 2. The second dialysate introduction line L1b is provided with the dialysate introduction pump P2, which is a peristaltic pump that delivers liquid by squeezing a flexible tube forming a flow route for the dialysate. When the dialysate introduction pump P2 is activated, a rotor rotates and rollers squeeze the flexible tube in the lengthwise direction. Thus, the dialysate stored in the dialysate temporary chamber K2 can be delivered to and introduced into the dialyzer 2.

The second dialysate introduction line L1b according to the present embodiment is further provided with the heating device H1 for heating the dialysate. The heating device H1 is a heater capable of heating the dialysate to be introduced from the dialysate temporary chamber K2 into the dialyzer 2. A heating bag 7 is attachable to the heating device H1. The heating bag 7 has a flow route obtained by, for example, fusing two flexible sheets to each other. The flow route has connecting portions at one end and the other end thereof, respectively, where the flow route is connectable to the second dialysate introduction line Db.

The first substitution line L2a is made of a flexible tube allowing substitution fluid stored in the substitution-fluid bag B2 (the substitution-fluid storage) to flow into the substitution-fluid temporary chamber K1. The first substitution line L2a has one end connected to the bottom of the substitution-fluid bag B2 (the substitution-fluid storage), and the other end connected to the bottom of the substitution-fluid temporary chamber K1. The substitution-fluid bag B2 stores a predetermined amount of substitution fluid to be fed to the blood circuit 1. As illustrated in FIGS. 2 and 3, the substitution-fluid bag B2 is supported at a predetermined height position by the supporting unit Q attached to the apparatus body. The substitution-fluid temporary chamber K1 stores the substitution fluid received from the substitution-fluid bag B2 (the substitution-fluid storage) and is a case with a smaller capacity than the substitution-fluid bag B2.

The first substitution line L2a is provided with the substitution-fluid transfer pump P6, which is a peristaltic pump that delivers liquid by squeezing a flexible tube forming a flow route for the substitution fluid. When the substitution-fluid transfer pump P6 is activated, a rotor rotates and rollers squeeze the flexible tube in the lengthwise direction. Thus, the substitution fluid stored in the substitution-fluid bag B2 can be delivered to and stored in the substitution-fluid temporary chamber K1.

The second substitution line L2b is made of a flexible tube that allows the substitution fluid stored in the substitution-fluid temporary chamber K1 to flow into the blood circuit 1 through the pre-substitution line L2c or the post-substitution line L2d. The second substitution line L2b has one end connected to the bottom of the substitution-fluid temporary chamber K1, and the other end connected to the pre-substitution line L2c and to the post-substitution line L2d. The second substitution line L2b is provided with the first substitution pump P3, which is a peristaltic pump that delivers liquid by squeezing a flexible tube forming a flow route for the substitution fluid. When the first substitution pump P3 is activated, a rotor rotates and rollers squeeze the flexible tube in the lengthwise direction. Thus, the substitution fluid stored in the substitution-fluid temporary chamber K1 can be delivered for substitution to the arterial blood circuit 1a through the pre-substitution line L2c or to the venous blood circuit 1b through the post-substitution line L2d.

The second substitution line L2b according to the present embodiment is further provided with the heating device H2 for heating the substitution fluid. The heating device H2 is a heater capable of heating the substitution fluid to be introduced from the substitution-fluid temporary chamber K1 into the blood circuit 1. The heating bag 7 is attachable to the heating device H2. The heating bag 7 has a flow route obtained by, for example, fusing two flexible sheets to each other. The flow route has connecting portions at one end and the other end thereof, respectively, where the flow route is connectable to the second substitution line L2b.

The second substitution line L2b is further provided with an air-trap chamber 8 at a position between the heating device H2 and the arterial blood circuit 1a or the venous blood circuit 1b. The air-trap chamber 8 is capable of trapping bubbles in the substitution fluid. The bubbles in the substitution fluid heated by the heating device H2 are trapped in the air-trap chamber 8 and are therefore prevented from flowing into the blood circuit 1. The air-trap chamber 8 is provided at the top thereof with a connection line L4 to which the pressure sensor Pb is attached. Therefore, the fluid pressure of the substitution fluid flowing in the second substitution line L2b is detectable through an air layer in the air-trap chamber 8. The connection line L4 is provided with an air filter F4.

The pre-substitution line L2c is a flow route through which the substitution fluid is introduced into the arterial blood circuit 1a for pre-substitution. The pre-substitution line L2c has one end connected to the second substitution line L2b, and the other end connected to a position of the arterial blood circuit 1a that is between the blood pump P1 and the dialyzer 2. When the first substitution pump P3 is activated and the substitution fluid is delivered from the substitution-fluid temporary chamber K1 through the second substitution line L2b, the substitution fluid flows through the pre-substitution line L2c into the arterial blood circuit 1a.

The post-substitution line L2d is a flow route through which the substitution fluid is introduced into the venous blood circuit 1b for post-substitution. The post-substitution line L2d has one end connected to the second substitution line L2b, and the other end connected to the air-trap chamber 3 provided to the venous blood circuit 1b. When the first substitution pump P3 is activated and the substitution fluid is delivered from the substitution-fluid temporary chamber K1 through the second substitution line L2b, the substitution fluid flows through the post-substitution line L2d into the venous blood circuit 1b.

The pre-substitution line L2c according to the present embodiment is provided with the second substitution pump P8, which is a peristaltic pump that delivers liquid by squeezing a flexible tube forming a flow route for the substitution fluid. The post-substitution line L2d is provided with a check valve V1 that allows the substitution fluid to flow toward the blood circuit 1 but prevents the substitution fluid from flowing toward the other side. The substitution pumps according to the present embodiment include the first substitution pump P3 provided to the substitution line (the second substitution line L2b) and the second substitution pump P8 provided to at least one of the pre-substitution line L2c and the post-substitution line L2d (in the present embodiment, the pre-substitution line L2c).

Hence, if the second substitution pump P8 is activated at substantially the same flow rate as that of the first substitution pump P3, the substitution fluid in the substitution-fluid temporary chamber K1 can be introduced into the arterial blood circuit 1a for pre-substitution. On the other hand, if the first substitution pump P3 is activated with the second substitution pump P8 stopped, the substitution fluid in the substitution-fluid temporary chamber K1 can be introduced into the venous blood circuit 1b for post-substitution. Furthermore, if the second substitution pump P8 is activated at a flow rate lower than that of the first substitution pump P3, the substitution fluid can be introduced into both the arterial blood circuit 1a and the venous blood circuit 1b for pre- and post-substitution with a ratio according to the flow rate of the second substitution pump P8. The control unit 6 is capable of changing the ratio between the amount of pre-substitution and the amount of post-substitution by controlling the first substitution pump P3 and the second substitution pump P8 in such a manner as to change the flow-rate ratio between the first substitution pump P3 and the second substitution pump P8.

The post-substitution line L2d is provided with the check valve V1. Therefore, even if a negative pressure is generated in the flow route between the first substitution pump P3 and the second substitution pump P8, the blood in the blood circuit 1 can be prevented from being taken into the post-substitution line L2d. Note that a negative pressure is generated in the flow route between the first substitution pump P3 and the second substitution pump P8 if the flow rate of the second substitution pump P8 is higher than the flow rate of the first substitution pump P3. Other possible embodiments are as follows: an embodiment in which the pre-substitution line L2c is provided with the check valve V1 while the post-substitution line L2d is provided with the second substitution pump P8, and an embodiment in which the pre-substitution line L2c and the post-substitution line L2d are each provided with the second substitution pump P8.

The blood purification apparatus further includes the pressure sensor Pb that detects the fluid pressure in a portion of the flow route for the substitution fluid, the portion being enclosed by the first substitution pump P3, the second substitution pump P8, and the check valve V1 in the second substitution line L2b (the substitution line), the pre-substitution line L2c, and the post-substitution line L2d. The control unit 6 corrects the driving speed of the first substitution pump P3 or the second substitution pump P8 in accordance with the fluid pressure detected by the pressure sensor Pb.

The first drain-liquid drain line L3a is made of a flexible tube that allows the drain liquid drained from the dialyzer 2 to flow into the drain-liquid temporary chamber K3. The first drain-liquid drain line L3a has one end connected to the dialysate delivery port 2d of the dialyzer 2, and the other end connected to the bottom of the drain-liquid temporary chamber K3. The drain-liquid temporary chamber K3 stores the drain liquid drained from the dialyzer 2 and is a case with a substantially equal capacity to those of the dialysate temporary chamber K2 and the substitution-fluid temporary chamber K1.

The first drain-liquid drain line L3a is provided with the drain-liquid drain pump P4, which is a peristaltic pump that delivers liquid by squeezing a flexible tube forming a flow route for the drain liquid. When the drain-liquid drain pump P4 is activated, a rotor rotates and rollers squeeze the flexible tube in the lengthwise direction. Thus, the drain liquid in the dialyzer 2 can be delivered to and stored in the drain-liquid temporary chamber K3.

The second drain-liquid drain line L3b is made of a flexible tube that allows the drain liquid stored in the drain-liquid temporary chamber K3 to be drained to the outside of the apparatus. The second drain-liquid drain line L3b has one end connected to the bottom of the drain-liquid temporary chamber K3, and the other end reaching a device, such as a processing device or a drain pan, provided on the outside of the apparatus. The second drain-liquid drain line L3b is provided with the drain-liquid transfer pump P7, which is a peristaltic pump that delivers liquid by squeezing a flexible tube forming a flow route for the drain liquid. The drain-liquid transfer pump P7 (a draining unit) is a pump that drains the drain liquid stored in the drain-liquid temporary chamber K3 to the outside of the apparatus at an arbitrary timing. When the drain-liquid transfer pump P7 is activated, a rotor rotates and rollers squeeze the flexible tube in the lengthwise direction. Thus, the drain liquid in the drain-liquid temporary chamber K3 can be drained to the outside of the apparatus.

As illustrated in FIGS. 3 and 4, the dialysate temporary chamber K2, the substitution-fluid temporary chamber K1, and the drain-liquid temporary chamber K3 are held by a holding unit N and are thus attached to the attaching unit D, which is to be described below. The top of each of the dialysate temporary chamber K2, the substitution-fluid temporary chamber K1, and the drain-liquid temporary chamber K3 is open to the atmosphere through a corresponding one of air filters F1 to F3. Therefore, if some liquid stored in the temporary chamber is discharged therefrom, some air is introduced into the temporary chamber. If some liquid flows into the temporary chamber, some air in the temporary chamber is discharged therefrom.

As illustrated in FIG. 2, the blood purification apparatus according to the present embodiment includes the supporting unit Q that supports the dialysate bag B1 and the substitution-fluid bag B2 at a predetermined height position; a monitor M that is capable of displaying information regarding the treatment and the like; an enclosure G that encloses the dialysate introduction pump P2, the first substitution pump P3, the drain-liquid drain pump P4, the dialysate transfer pump P5, the substitution-fluid transfer pump P6, the drain-liquid transfer pump P7, and the second substitution pump P8; and the attaching unit D.

The supporting unit Q is a pole-like member attached to the apparatus body and includes hanging portions Q1 capable of supporting the dialysate bag B1 and the substitution-fluid bag B2 at the predetermined height position, and a locking portion R operable in changing the height position. Specifically, the supporting unit Q according to the present embodiment is extendable and contractible in the lengthwise direction, so that the height position where the dialysate bag B1 and the substitution-fluid bag B2 are supported can be adjusted arbitrarily.

The locking portion R of the supporting unit Q is capable of locking and unlocking an upper part and a lower part of the supporting unit Q to and from each other. The height position of the hanging portions Q1 is adjustable in an unlocked state by sliding the upper part relative to the lower part. After the height position of the hanging portions Q1 is adjusted, the locking portion R is operated to lock the upper part of the supporting unit Q to the lower part, so that the dialysate bag B1 and the substitution-fluid bag B2 can be hung on the hanging portions.

The holding unit N holding the temporary chambers (the dialysate temporary chamber K2, the substitution-fluid temporary chamber K1, and the drain-liquid temporary chamber K3) is attachable to the attaching unit D. As illustrated in FIG. 5, the weight of the dialysate temporary chamber K2, the substitution-fluid temporary chamber K1, and the drain-liquid temporary chamber K3 is to be measured by the weighing device 4 (a weight sensor) attached to the back of the attaching unit D. Thus, the weight balance between the dialysate, the substitution fluid, and the drain liquid stored in the dialysate temporary chamber K2, the substitution-fluid temporary chamber K1, and the drain-liquid temporary chamber K3 is detectable in real time for monitoring.

The attaching unit D is further provided with the liquid-level sensor S1 that detects the reaching of the liquid surface in the dialysate temporary chamber K2 to a specified level (i.e., a situation where the amount of dialysate stored therein has reached a specified value), and the liquid-level sensor S2 that detects the reaching of the liquid surface in the substitution-fluid temporary chamber K1 to a specified level (i.e., a situation where the amount of substitution fluid stored therein has reached a specified value). Thus, a situation where the dialysate temporary chamber K2 or the substitution-fluid temporary chamber K1 has become full (a situation where the amount of dialysate or substitution fluid has reached a specified value or greater) is detectable.

The judging unit 5 judges whether or not a reference remaining amount is reached by the drain liquid in the drain-liquid temporary chamber from the result of detection by the weighing device 4 (the remaining-amount-detecting unit). The control unit 6 controls the draining unit. The control unit 6 controls various actuators such as the dialysate introduction pump P2, the first substitution pump P3, the drain-liquid drain pump P4, the dialysate transfer pump P5, the substitution-fluid transfer pump P6, the drain-liquid transfer pump P7, and the second substitution pump P8 in accordance with the value measured by the weighing device 4. The control unit 6 is a microcomputer or the like provided on the apparatus body. The control unit 6 according to the present embodiment executes an initialization process in which the amount of dialysate in the dialysate temporary chamber K2 and the amount of substitution fluid in the substitution-fluid temporary chamber K1 are increased to respective specified values or greater (a full state), and the amount of drain liquid in the drain-liquid temporary chamber K3 is reduced to a specified value or smaller (an initialized state) by draining the drain liquid with the drain-liquid transfer pump P7 (the draining unit); and a monitoring process in which the dialysate in the dialysate temporary chamber K2, the substitution fluid in the substitution-fluid temporary chamber K1, and the drain liquid in the drain-liquid temporary chamber K3 are weighed with the weighing device 4. Note that the initialized state of the drain-liquid temporary chamber K3 is desirably, but is not limited to, a state established immediately before the drain-liquid temporary chamber K3 becomes completely empty and may be specified by any value.

Specifically, in the monitoring process, the dialysate introduction pump P2 is activated to introduce the dialysate stored in the dialysate temporary chamber K2 into the dialyzer 2, the first substitution pump P3 (and the second substitution pump P8, according to need) is activated to introduce the substitution fluid stored in the substitution-fluid temporary chamber K1 into the blood circuit 1, and the drain-liquid drain pump P4 is activated to store the drain liquid drained from the dialyzer 2 in the drain-liquid temporary chamber K3. In this process, the dialysate transfer pump P5, the substitution-fluid transfer pump P6, and the drain-liquid transfer pump P7 are stopped.

In the monitoring process, the weight balance between the dialysate, the substitution fluid, and the drain liquid stored in the dialysate temporary chamber K2, the substitution-fluid temporary chamber K1, and the drain-liquid temporary chamber K3 is detectable in real time by the weighing device 4 for monitoring. Therefore, the weight balance between the dialysate, the substitution fluid, and the drain liquid can be set to a desired level by controlling the operation of the dialysate introduction pump P2, the first substitution pump P3 (and the second substitution pump P8), and the drain-liquid drain pump P4 in accordance with the value measured by the weighing device 4. Thus, normal treatment can be achieved.

In the above monitoring process, when it is detected that the total amount (accumulated amount) of flow generated by each of the dialysate introduction pump P2, the first substitution pump P3 (and the second substitution pump P8, according to need), and the drain-liquid drain pump P4 has reached a predetermined value and the dialysate temporary chamber K2 and the substitution-fluid temporary chamber K1 have been initialized (the amounts of liquids therein are reduced to the specified values or smaller) while the drain-liquid temporary chamber K3 has become full (the amount of liquid therein is increased to the specified value or greater), the operation is shifted to the initialization process.

In the initialization process, while the dialysate introduction pump P2, the first substitution pump P3 (and the second substitution pump P8, according to need), and the drain-liquid drain pump P4 are kept active, the dialysate transfer pump P5, the substitution-fluid transfer pump P6, and the drain-liquid transfer pump P7 are activated. Thus, the active dialysate transfer pump P5 causes the dialysate in the dialysate bag B1 to flow into and be stored in the dialysate temporary chamber K2, the active substitution-fluid transfer pump P6 causes the substitution fluid in the substitution-fluid bag B2 to flow into and be stored in the substitution-fluid temporary chamber K1, and the active drain-liquid transfer pump P7 causes the drain liquid in the drain-liquid temporary chamber K3 to be drained to the outside of the apparatus.

Note that the initialization may be executed by temporarily stopping the operation of the dialysate introduction pump P2, the first substitution pump P3, and the drain-liquid drain pump P4 and then activating the dialysate transfer pump P5, the substitution-fluid transfer pump P6, and the drain-liquid transfer pump P7. In such a manner, the amount of drain liquid drained in the initialization can be grasped easily.

Furthermore, the liquid-level sensors S1 and S2 are provided for detecting the liquid surfaces in the dialysate temporary chamber K2 and the substitution-fluid temporary chamber K1, respectively. Therefore, the reaching of the amounts of dialysate and substitution fluid stored in the dialysate temporary chamber K2 and the substitution-fluid temporary chamber K1 to the respective specified levels is detectable. In such a case, since no liquid-level sensor that detects the liquid surface in the drain-liquid temporary chamber K3 is provided, a situation where the drain-liquid temporary chamber K3 has been initialized (the reaching of the amount of liquid to a specified value or smaller) cannot be detected directly.

Hence, according to the present embodiment, the reaching of the amounts of dialysate and substitution fluid to the specified values is detected in the initialization process by using the liquid-level sensors S1 and S2. Then, after the reaching of the amounts of dialysate and substitution fluid to the specified values (the full state) is detected, if the total weight of the dialysate, the substitution fluid, and the drain liquid in the dialysate temporary chamber K2, the substitution-fluid temporary chamber K1, and the drain-liquid temporary chamber K3 that is measured by the weighing device 4 (the value measured by the weighing device 4) is reduced to a specified value or smaller (the initialized state), the draining of the drain liquid by the drain-liquid transfer pump P7 (the draining unit) is ended to shift the operation to the monitoring process.

Thus, even if no liquid-level sensor that detects the liquid surface in the drain-liquid temporary chamber K3 is provided, the draining of the drain liquid can be ended when the drain-liquid temporary chamber K3 is initialized (when the amount of liquid is reduced to the specified value or smaller). Such a configuration can prevent the occurrence of insufficient draining of the drain liquid, or mixing of air due to lowering of the drain-liquid surface to the first drain-liquid drain line L3a or the second drain-liquid drain line L3b with continued operation of the drain-liquid transfer pump P7 even after the initialization.

In addition to the above condition, in the initialization process, if the total amount of flow (the total number of revolutions of the rotor) generated by the drain-liquid transfer pump P7 (the draining unit) has reached the total amount of flow (the total number of revolutions of the rotor) generated by the drain-liquid drain pump P7 in the previous monitoring process, the control unit 6 may shift the operation to the monitoring process. In such a configuration, the drain liquid in the drain-liquid temporary chamber K3 can be drained more correctly.

Now, a sequence of controlling the initialization process executed by the control unit 6 according to the present embodiment will be described with reference to the flow chart illustrated in FIG. 6 and the timing chart illustrated in FIG. 7.

When the initialization process is started (at a time point T1 in FIG. 7), while the dialysate introduction pump P2, the first substitution pump P3 (and the second substitution pump P8, according to need), and the drain-liquid drain pump P4 are kept active, the dialysate transfer pump P5, the substitution-fluid transfer pump P6, and the drain-liquid transfer pump P7 are activated (S1). Thus, the dialysate in the dialysate bag B1 is fed into and stored in the dialysate temporary chamber K2, and the substitution fluid in the substitution-fluid bag B2 is fed into and stored in the substitution-fluid temporary chamber K1 (a feeding operation). Furthermore, the active drain-liquid transfer pump P7 causes the drain liquid in the drain-liquid temporary chamber K3 to be drained to the outside of the apparatus (a discharge operation).

In the above initialization process, since the dialysate introduction pump P2, the first substitution pump P3 (and the second substitution pump P8, according to need), and the drain-liquid drain pump P4 are active, not only the feeding operation and the draining operation but also the introduction of the dialysate into the dialyzer 2, the introduction of the substitution fluid into the blood circuit 1, and the draining of the drain liquid from the dialyzer 2 are performed. Therefore, the blood purification treatment is continued.

Then, in S2, whether or not the liquid surfaces in the dialysate temporary chamber K2 and the substitution-fluid temporary chamber K1 have been detected by the liquid-level sensors S1 and S2 (whether or not the amounts of dialysate and substitution fluid have reached the specified values indicating the full state) is judged. If it is judged that the liquid surfaces have been detected, the process proceeds to S3, where the dialysate transfer pump P5 and the substitution-fluid transfer pump P6 are stopped, whereby the feeding operation is ended (at a time point T2 in FIG. 7). Subsequently, in S4, whether or not the total weight of the dialysate, the substitution fluid, and the drain liquid in the dialysate temporary chamber K2, the substitution-fluid temporary chamber K1, and the drain-liquid temporary chamber K3 that is measured by the weighing device 4 (the value measured by the weighing device 4) has reached a value smaller than the specified value (indicating the initialized state) is judged. If it is judged that the total weight has reached a value smaller the specified value, the process proceeds to S5, where the drain-liquid transfer pump P7 is stopped, whereby the discharge operation is ended (at a time point T3 in FIG. 7). Then, in S6, the operation is shifted to the monitoring process.

Now, a sequence of controlling the monitoring process executed by the control unit 6 according to the present embodiment will be described with reference to the flow chart illustrated in FIG. 8 and the timing chart illustrated in FIG. 7.

When the monitoring process is started (at a time point T3 in FIG. 7), while the dialysate introduction pump P2, the first substitution pump P3 (and the second substitution pump P8, according to need), and the drain-liquid drain pump P4 are kept active, the dialysate transfer pump P5, the substitution-fluid transfer pump P6, and the drain-liquid transfer pump P7 are kept stopped.

In the above state, while the feeding operation for the dialysate temporary chamber K2 and the substitution-fluid temporary chamber K1 and the discharge operation for the drain-liquid temporary chamber K3 are kept stopped, the introduction of the dialysate into the dialyzer 2, the introduction of the substitution fluid into the blood circuit 1, and the draining of the drain liquid from the dialyzer 2 are performed. Therefore, the blood purification treatment is continued. In S1, whether or not the amounts of activation (the total numbers of revolutions of the rotors) of the dialysate introduction pump P2, the first substitution pump P3 (and the second substitution pump P8, according to need), and the drain-liquid drain pump P4 have reached respective specified values (i.e., values specified for making the dialysate temporary chamber K2 and the substitution-fluid temporary chamber K1 full) is judged. If it is judged that the amounts of activation have reached the specified values, the process proceeds to S2 so that the operation is shifted to the initialization process.

According to the present embodiment, the initialization process is executed in which the drain liquid in the drain-liquid temporary chamber K3 is drained to the outside of the apparatus until the reference remaining amount is reached. The initialization process is ended if it is judged by the judging unit 5 that the reference remaining amount is reached by the drain liquid in the drain-liquid temporary chamber K3. Therefore, introduction of air into the drain-liquid temporary chamber that may occur with the execution of the initialization process can be suppressed.

Furthermore, the monitoring process is executed in which the amount of drain liquid in the drain-liquid temporary chamber K3 is monitored by the weighing device 4 (the remaining-amount-detecting unit). The operation is shifted from the initialization process to the monitoring process if it is judged by the judging unit 5 that the reference remaining amount is reached by the drain liquid in the drain-liquid temporary chamber K3. Therefore, smooth shifting from the initialization process to the monitoring process can be achieved. The control unit 6 according to the present embodiment alternately executes the initialization process and the monitoring process. Therefore, smooth repetition of the initialization process and the monitoring process can be achieved, The judging unit 5 judges whether or not the reference remaining amount is reached by the drain liquid in the drain-liquid temporary chamber K3 in the initialization process from the result of measurement by the weighing device 4 while the feeding of the feeding liquids (the substitution fluid and the dialysate) to the respective feeding-liquid temporary chambers (the substitution-fluid temporary chamber K1 and the dialysate temporary chamber K2) is stopped. Therefore, in the initialization process, the situation where the drain-liquid temporary chamber K3 has been initialized can be grasped correctly.

The remaining-amount-detecting unit further includes the liquid-level sensors (S1 and S2) that detect the surfaces of the feeding liquids stored in the feeding-liquid temporary chambers. The judging unit 5 judges whether or not a reference feeding amount is reached by each of the feeding liquids in a corresponding one of the feeding-liquid temporary chambers in the initialization process from the result of detection by a corresponding one of the liquid-level sensors (S1 and S2). The control unit stops the feeding of the feeding liquid to the feeding-liquid temporary chamber (the substitution-fluid temporary chamber K1 or the dialysate temporary chamber K2) if it is judged by the judging unit 5 that the reference feeding amount is reached by the feeding liquid in the feeding-liquid temporary chamber (the substitution-fluid temporary chamber K1 or the dialysate temporary chamber K2) in the initialization process. Therefore, in the initialization process, the situation where the dialysate temporary chamber K2 and the substitution-fluid temporary chamber K1 have become full can be grasped correctly, and the situation where the drain-liquid temporary chamber K3 has been initialized can be grasped correctly.

If the reference feeding amount is reached by the feeding liquid in the feeding-liquid temporary chambers (K1 or K2), the feeding-liquid delivery pump (P5 or P6) may be controlled at substantially the same flow rate as the flow rate of the dialysate introduction pump P2 or the first substitution pump P3. In such a case, the judging unit judges whether or not the reference remaining amount is reached by the drain liquid in the drain-liquid temporary chamber K3 in the initialization process from the result of measurement by the weighing device 4 while the amount of feeding liquid in the feeding-liquid temporary chamber (K1 or K2) is maintained at a constant value. Specifically, since the amount of feeding liquid to be fed to the feeding-liquid temporary chamber (K1 or K2) and the amount of feeding liquid to be discharged therefrom are made substantially the same, the liquid level (the amount of liquid) in the feeding-liquid temporary chamber (K1 or K2) can be maintained at a constant level. Therefore, even with a weighing device that measures the total weight of the feeding-liquid temporary chamber (K1 or K2) and the drain-liquid temporary chamber K3, the amount of liquid remaining in the drain-liquid temporary chamber K3 can be grasped, if factors that change the weight of the feeding-liquid temporary chamber (K1 or K2) are ignored.

The draining unit is provided as the drain-liquid transfer pump P7 that drains the drain liquid stored in the drain-liquid temporary chamber K3 to the outside of the apparatus by transferring the drain liquid. Therefore, smooth draining of the drain liquid from the drain-liquid temporary chamber K3 in the initialization process can be achieved. Furthermore, if the flow rate of the drain-liquid transfer pump P7 is controlled, the duration of draining the drain liquid can be adjusted arbitrarily.

The blood purification apparatus further includes the drain-liquid drain pump P4 provided to the first drain-liquid drain line L3*a* and that delivers the dialysate from the dialyzer 2 to the drain-liquid temporary chamber K3. Furthermore, the draining unit is provided as the drain-liquid transfer pump P7 that drains the drain liquid stored in the drain-liquid temporary chamber K3 to the outside of the apparatus by transferring the drain liquid. Furthermore, if the total amount of flow generated by the drain-liquid drain pump P4 in the previous monitoring process is reached by the total amount of flow generated by the drain-liquid transfer pump P7 in the initialization process, the control unit 6 shifts the operation to the monitoring process. Therefore, in combination with the weight condition, the situation where the drain-liquid temporary chamber K3 has been initialized can be grasped more accurately.

The drain-liquid transfer pump P7 is a peristaltic pump that delivers liquid by squeezing a flexible tube forming a flow route for the drain liquid. Therefore, the second drain-liquid drain line L3*b* can be closed by the drain-liquid transfer pump P7, with no need to provide any separate clamp unit or the like. Furthermore, the draining unit is provided to the second drain-liquid drain line L3*b* extending from the bottom of the drain-liquid temporary chamber K3. Therefore, the error in the measurement by the measuring unit can be made smaller than in a case where the drain-liquid transfer pump P7 is provided to another flow route extending from the top of the drain-liquid temporary chamber K3. Specifically, it is possible to provide a gas flow route extending from the top of the drain-liquid temporary chamber K3 so that the drain liquid in the drain-liquid temporary chamber K3 is drained to the outside of the apparatus by sending air thereinto with the drain-liquid transfer pump P7. In such a case, however, the weight of the drain-liquid transfer pump P7 may affect the value measured by the weighing device 4, leading to an error. Therefore, if the drain-liquid transfer pump P7 is provided to the second drain-liquid drain line L3*b* extending from the bottom of the drain-liquid temporary chamber K3 as in the present embodiment, the error in the measurement by the weighing device 4 can be reduced.

While some embodiments have been described above, the present invention is not limited thereto. For example, an embodiment illustrated in FIG. 9 may be employed in which a connection line L3*c* is provided in such a manner as to extend from the bottom of the drain-liquid temporary chamber K3, and the first drain-liquid drain line L3*a* and the second drain-liquid drain line L3*b* are connected to the connection line L3*c*. In such an embodiment, the drain liquid in the dialyzer 2 flows through the first drain-liquid drain line L3*a* and the connection line L3*c* into the drain-liquid temporary chamber K3, and the drain liquid thus stored in the drain-liquid temporary chamber K3 flows through the connection line L3*c* and the second drain-liquid drain line L3*b* and is drained to the outside of the apparatus.

An embodiment illustrated in FIG. 10 may also be employed in which the draining unit provided to the second drain-liquid drain line L3*b* and that drains the drain liquid stored in the drain-liquid temporary chamber K3 to the outside of the apparatus at an arbitrary timing is an electromagnetic valve V3 that is controlled to be opened or closed by the control unit 6. In such an embodiment, the initialization process is executed with the electromagnetic valve V3 being open so as to drain the drain liquid to the outside of the apparatus. Thus, the amount of drain liquid in the drain-liquid temporary chamber K3 can be reduced to the specified value or smaller (the initialized state). The electromagnetic valve V3 may be replaced with another clamp unit capable of opening and closing the flow route as the second drain-liquid drain line L3*b*.

The above embodiments each concern a case where a single weighing device 4 measures the total weight of the dialysate, the substitution fluid, and the drain liquid in the dialysate temporary chamber K2, the substitution-fluid temporary chamber K1, and the drain-liquid temporary chamber K3 and detects the weight balance therebetween for monitoring. Alternatively, plural weighing devices may be provided for measuring the respective weights of the dialysate, the substitution fluid, and the drain liquid in the dialysate temporary chamber K2, the substitution-fluid temporary chamber K1, and the drain-liquid temporary chamber K3.

The weighing device 4 may be replaced with a measuring unit of another type that measures the amount of liquid stored in the drain-liquid temporary chamber K3, and may include a liquid-level sensor that detects the liquid surface in the drain-liquid temporary chamber K3. In the initialization process, the situation where the amounts of dialysate and substitution fluid are increased to the specified values (the full state) may be detected with reference to the total amounts of flow (the total numbers of revolutions of the rotors) generated by the dialysate transfer pump P5 and the substitution-fluid transfer pump P6. In such a case, the liquid-level sensors S1 and S2 can be omitted. The dialysate bag B1 and the substitution-fluid bag B2, which are each a flexible case, may be replaced with a dialysate storage and a substitution-fluid storage each being a hard case, a liquid tank, or the like.

Yet another embodiment may be employed in which a liquid-level sensor (any type such as an optical type, a capacitance type, or an ultrasonic type) is provided to the drain-liquid temporary chamber K3 or the second drain-liquid drain line L3b, and the control unit ends the draining process (initialization process) if it is detected by the liquid-level sensor that the amount of liquid remaining in the drain-liquid temporary chamber K3 is reduced to a specified value or smaller. A control sequence executed in such an embodiment will now be described with reference to the flow chart illustrated in FIG. 11. When the draining process is started, a drain-liquid-controlling step S1 is performed. Subsequently, whether or not any air or a reduction in the remaining amount of liquid to the specified value or smaller is detected by the liquid-level sensor is judged (S2). The drain-liquid-controlling step S1 is continued until any air or a reduction in the remaining amount of liquid to the specified value or smaller is detected by the liquid-level sensor. If any air or a reduction in the remaining amount of liquid to the specified value or smaller is detected by the liquid-level sensor, the discharge process is ended.

Yet another embodiment may be employed in which a positive displacement pump (including a peristaltic pump) or a flowmeter (such as a vortex flowmeter or an ultrasonic flowmeter) is provided to the second drain-liquid drain line L3b, the amount of drain liquid drained from the drain-liquid temporary chamber K3 through the second drain-liquid drain line L3b to the outside of the apparatus is calculated, the amount of drain liquid remaining in the drain-liquid temporary chamber K3 is detected as the difference from the amount of drain liquid introduced into the drain-liquid temporary chamber K3 through the first drain-liquid drain line L3a, and the control unit ends the draining process if it is judged that the amount of drain liquid remaining is reduced to a specified value or smaller.

A control sequence executed in such an embodiment will now be described with reference to the flow chart illustrated in FIG. 12. When the draining process is started, a drain-liquid-controlling step S1 is performed. Subsequently, the amount of liquid remaining in the drain-liquid temporary chamber K3 is calculated by using the positive displacement pump or the flowmeter (S2). Then, whether or not the calculated remaining amount is reduced to the specified value or smaller is judged (S3). The drain-liquid-controlling step S1 is continued until the amount of liquid remaining in the drain-liquid temporary chamber K3 is reduced to the specified value. If it is judged that the remaining amount is reduced to the specified value or smaller, the draining process is ended.

The blood purification apparatus may have other additional functions or the like, as long as a draining process in which a draining unit is controlled such that drain liquid stored in a drain-liquid temporary chamber is drained to the outside of the apparatus is executed, and the draining process is ended if it is judged by a judging unit that a reference remaining amount is reached by the drain liquid in the drain-liquid temporary chamber.

REFERENCE SIGN LIST 1 blood circuit
1a arterial blood circuit
1b venous blood circuit
2 dialyzer (blood purifier)
3 air-trap chamber
4 weighing device (remaining-amount-detecting unit) (measuring unit)
5 judging unit
6 control unit
7 heating bag
8 air-trap chamber
K1 substitution-fluid temporary chamber (feeding-liquid temporary chamber)
K2 dialysate temporary chamber (feeding-liquid temporary chamber)
K3 drain-liquid temporary chamber
B1 dialysate bag (dialysate storage) (feeding-liquid storage)
B2 substitution-fluid bag (substitution-fluid storage) (feeding-liquid storage)
L1a first dialysate introduction line (feeding-liquid introduction line)
L1b second dialysate introduction line
L2a first substitution line
L2b second substitution line
L2c pre-substitution line
L2d post-substitution line
L3a first drain-liquid drain line
L3b second drain-liquid drain line
P1 blood pump
P2 dialysate introduction pump
P3 first substitution pump
P4 drain-liquid drain pump
P5 dialysate transfer pump
P6 substitution-fluid transfer pump
P7 drain-liquid transfer pump (draining unit)
P8 second substitution pump
H1 first heating device
H2 second heating device
S1, S2 liquid-level sensor
Pa, Pb pressure sensor
D attaching unit
Q supporting unit

What is claimed is:

1. A blood purification apparatus comprising:
a drain-liquid temporary chamber that stores drain liquid drained from a blood purifier that purifies blood of a patient;
a first drain-liquid drain line through which the drain liquid flows into the drain-liquid temporary chamber;
a second drain-liquid drain line through which the drain liquid stored in the drain-liquid temporary chamber is drained to an outside of the blood purification apparatus;
a draining unit provided to the second drain-liquid drain line and that drains the drain liquid stored in the drain-liquid temporary chamber to an outside of the blood purification apparatus, wherein the draining unit includes a drain-liquid transfer pump located between the drain-liquid temporary chamber and the outside of the blood purification apparatus, to drain the drain liquid stored in the drain-liquid temporary chamber to the outside of the blood purification apparatus by transferring the drain liquid;
a remaining-amount-detecting unit that detects an amount of drain liquid remaining in the drain-liquid temporary chamber;
a drain-liquid drain pump located within the first drain-liquid drain line between the blood purifier and the drain-liquid temporary chamber and to deliver dialysate from the blood purifier to the drain-liquid temporary chamber;
a judging unit that judges whether or not a reference remaining amount is reached by the drain liquid in the drain-liquid temporary chamber from a result of detection by the remaining-amount-detecting unit; and
a control unit that controls the draining unit,
wherein the control unit executes a draining process in which the draining unit is controlled such that the drain liquid in the drain-liquid temporary chamber is drained to the outside of the blood purification apparatus, and the draining process is ended if it is judged by the judging unit that the reference remaining amount is reached by the drain liquid in the drain-liquid temporary chamber; and
wherein if a total amount of flow generated by the drain-liquid drain pump in a previous monitoring process is reached by a total amount of flow generated by the drain-liquid transfer pump in the draining process, the control unit shifts operation to a monitoring process.

2. The blood purification apparatus according to claim 1, wherein the control unit further executes a monitoring process in which the amount of drain liquid in the drain-liquid temporary chamber is monitored by the remaining-amount-detecting unit, and operation is shifted from the draining process to the monitoring process if it is judged by the judging unit that the reference remaining amount is reached by the drain liquid in the drain-liquid temporary chamber.

3. The blood purification apparatus according to claim 1, wherein the control unit alternately executes the draining process and the monitoring process.

4. The blood purification apparatus according to claim 1, further comprising:
a feeding-liquid storage that stores, as feeding liquid, dialysate to be fed to the blood purifier or substitution fluid to be fed through the blood purifier to a blood circuit through which the blood of the patient circulates;
a feeding-liquid temporary chamber that stores the feeding liquid received from the feeding-liquid storage; and
a feeding-liquid introduction line through which the feeding liquid stored in the feeding-liquid storage flows into the feeding-liquid temporary chamber,
wherein the remaining-amount-detecting unit includes a weighing device that measures a total weight of the feeding-liquid temporary chamber and the drain-liquid temporary chamber,
wherein the draining process is an initialization process in which the amount of drain liquid in the drain-liquid temporary chamber and an amount of feeding liquid in the feeding-liquid temporary chamber are initialized by continuing the draining until the reference remaining amount is reached by the drain liquid in the drain-liquid temporary chamber while continuing feeding until a reference feeding amount is reached by the feeding liquid in the feeding-liquid temporary chamber, and
wherein the judging unit judges whether or not the reference remaining amount is reached by the drain liquid in the drain-liquid temporary chamber in the initialization process from a result of measurement by the weighing device while the feeding of the feeding liquid to the feeding-liquid temporary chamber is stopped.

5. The blood purification apparatus according to claim 4, wherein the remaining-amount-detecting unit further includes a liquid-level sensor that detects a surface of the feeding liquid in the feeding-liquid temporary chamber,
wherein the judging unit judges whether or not the reference feeding amount is reached by the feeding liquid in the feeding-liquid temporary chamber in the initialization process from a result of detection by the liquid-level sensor, and
wherein the control unit stops the feeding of the feeding liquid to the feeding-liquid temporary chamber if it is judged by the judging unit that the reference feeding amount is reached by the feeding liquid in the feeding-liquid temporary chamber in the initialization process.

6. The blood purification apparatus according to claim 1, further comprising:
a feeding-liquid storage that stores, as feeding liquid, dialysate to be fed to the blood purifier or substitution fluid to be fed through the blood purifier to a blood circuit through which the blood of the patient circulates;
a feeding-liquid temporary chamber that stores the feeding liquid received from the feeding-liquid storage; and
a feeding-liquid introduction line through which the feeding liquid stored in the feeding-liquid storage flows into the feeding-liquid temporary chamber,
wherein the remaining-amount-detecting unit includes a weighing device that measures a total weight of the feeding-liquid temporary chamber and the drain-liquid temporary chamber,
wherein the draining process is an initialization process in which the amount of drain liquid in the drain-liquid temporary chamber and an amount of feeding liquid in the feeding-liquid temporary chamber are initialized by continuing the draining until the reference remaining amount is reached by the drain liquid in the drain-liquid temporary chamber while continuing feeding until a reference feeding amount is reached by the feeding liquid in the feeding-liquid temporary chamber, and
wherein the judging unit judges whether or not the reference remaining amount is reached by the drain liquid in the drain-liquid temporary chamber in the initialization process from a result of measurement by the weighing device while the amount of feeding liquid in the feeding-liquid temporary chamber is maintained at a constant value.

7. The blood purification apparatus according to claim 1, wherein the drain-liquid transfer pump is a peristaltic pump that delivers liquid by squeezing a flexible tube forming a flow route for the drain liquid.

8. The blood purification apparatus according to claim 1, wherein the draining unit is provided to the second drain-liquid drain line, the second drain-liquid drain line extending from a bottom of the drain-liquid temporary chamber.

* * * * *